(12) United States Patent
Lintula et al.

(10) Patent No.: US 10,595,915 B2
(45) Date of Patent: Mar. 24, 2020

(54) BONE IMPLANT DEVICES, INSTRUMENTS AND METHODS OF USE

(71) Applicant: Paragon 28, Inc., Englewood, CO (US)

(72) Inventors: Eric Lintula, Parker, CO (US); Laura Zagrocki Brinker, Denver, CO (US); Albert Dacosta, Lone Tree, CO (US)

(73) Assignee: Paragon 28, Inc., Englewood, CO (US)

( * ) Notice: Subject to any disclaimer, the term of this patent is extended or adjusted under 35 U.S.C. 154(b) by 10 days.

(21) Appl. No.: 15/920,615

(22) Filed: Mar. 14, 2018

(65) Prior Publication Data
US 2018/0256219 A1 Sep. 13, 2018

Related U.S. Application Data

(63) Continuation of application No. PCT/US2018/022079, filed on Mar. 12, 2018.

(60) Provisional application No. 62/469,478, filed on Mar. 10, 2017.

(51) Int. Cl.
| | |
|---|---|
| *A61B 17/72* | (2006.01) |
| *A61B 17/88* | (2006.01) |
| *A61B 17/92* | (2006.01) |
| *A61B 17/56* | (2006.01) |

(52) U.S. Cl.
CPC .......... *A61B 17/7291* (2013.01); *A61B 17/72* (2013.01); *A61B 17/8872* (2013.01); *A61B 17/92* (2013.01); *A61B 2017/564* (2013.01)

(58) Field of Classification Search
CPC . A61B 17/7291; A61B 17/72; A61B 17/8872; A61B 17/92; A61B 2017/564
USPC .................................. 606/62, 301, 76, 99
See application file for complete search history.

(56) References Cited

U.S. PATENT DOCUMENTS

| | | | |
|---|---|---|---|
| 4,246,662 | A | 1/1981 | Pastrick |
| 5,207,712 | A | 5/1993 | Cohen |
| 5,480,447 | A | 1/1996 | Skiba |
| 6,008,431 | A | 12/1999 | Caldarise et al. |
| 7,041,106 | B1 | 5/2006 | Carver et al. |
| 8,021,367 | B2 | 9/2011 | Bourke et al. |
| 8,100,983 | B2 | 1/2012 | Schulte |
| 8,529,611 | B2 | 9/2013 | Champagne et al. |

(Continued)

OTHER PUBLICATIONS

International Search Report and Written Opinion of the International Searching Authority for PCT/US2018/022079, dated May 25, 2018, 11 pages.

(Continued)

*Primary Examiner* — Pedro Philogene
*Assistant Examiner* — David C Comstock
(74) *Attorney, Agent, or Firm* — Heslin Rothenberg Farley & Mesiti P.C.; Jacquelyn A. Graff, Esq.

(57) ABSTRACT

Implants, devices, instruments, systems and methods for correcting bone deformities in the extremities are disclosed. Specifically, implants, devices, instruments, systems and methods used for hammertoe procedures are disclosed. The implant insertion system including an insertion instrument and an implant. The insertion instrument including a first end, a second end, and an opening extending into the insertion instrument from the second end. The implant including a first portion at a first end, a second portion at a second end, and an intermediate portion coupling the first portion to the second portion. The first portion being received within the opening of the insertion instrument.

20 Claims, 18 Drawing Sheets

(56) References Cited

U.S. PATENT DOCUMENTS

| | | | |
|---|---|---|---|
| 8,597,337 | B2 | 12/2013 | Champagne |
| 8,685,024 | B2 | 4/2014 | Roman |
| 8,715,326 | B2 | 5/2014 | Champagne et al. |
| 8,834,572 | B2 | 9/2014 | Averous et al. |
| 8,864,804 | B2 | 10/2014 | Champagne et al. |
| 8,888,778 | B2 | 11/2014 | Roman |
| 10,058,431 | B2 * | 8/2018 | Tyber .................... A61B 17/70 |
| 2002/0169066 | A1 | 11/2002 | Cassidy et al. |
| 2006/0206044 | A1 | 9/2006 | Simon |
| 2007/0093841 | A1 | 4/2007 | Hoogland |
| 2007/0156241 | A1 | 7/2007 | Reiley et al. |
| 2007/0270711 | A1 | 11/2007 | Gil et al. |
| 2008/0065215 | A1 | 3/2008 | Reiley |
| 2010/0168798 | A1 | 7/2010 | Clineff et al. |
| 2010/0266979 | A1 * | 10/2010 | Karmon ............... A61B 17/025 433/80 |
| 2011/0054545 | A1 | 3/2011 | Champagne et al. |
| 2012/0065692 | A1 | 3/2012 | Champagne et al. |
| 2012/0221049 | A1 | 8/2012 | Blain |
| 2012/0323243 | A1 | 12/2012 | Moon et al. |
| 2013/0066383 | A1 | 3/2013 | Anderson et al. |
| 2013/0123862 | A1 | 5/2013 | Anderson et al. |
| 2013/0131822 | A1 | 5/2013 | Lewis et al. |
| 2013/0317559 | A1 | 11/2013 | Leavitt et al. |
| 2013/0325077 | A1 | 12/2013 | Champagne et al. |
| 2013/0338785 | A1 | 12/2013 | Wong |
| 2014/0107712 | A1 | 4/2014 | Fallin et al. |
| 2014/0188239 | A1 | 7/2014 | Cummings |
| 2014/0222091 | A1 | 8/2014 | Champagne et al. |
| 2014/0276825 | A1 | 9/2014 | Brown et al. |
| 2014/0277183 | A1 | 9/2014 | Stalcup et al. |
| 2015/0073413 | A1 | 3/2015 | Palmer et al. |
| 2015/0112341 | A1 | 4/2015 | Penzimer et al. |
| 2015/0142066 | A1 | 5/2015 | Shemwell et al. |
| 2015/0150607 | A1 | 6/2015 | Chen et al. |
| 2015/0164563 | A1 | 6/2015 | Lewis et al. |
| 2015/0190147 | A1 | 7/2015 | Ferragamo et al. |
| 2015/0374503 | A1 | 12/2015 | Lovick et al. |
| 2016/0030095 | A1 | 2/2016 | Roman et al. |
| 2016/0045324 | A1 | 2/2016 | Austin et al. |
| 2016/0287407 | A1 | 10/2016 | Patrick et al. |
| 2017/0000618 | A1 * | 1/2017 | Tyber .................... A61F 2/4225 |
| 2018/0021145 | A1 * | 1/2018 | Seavey ................. A61F 2/4225 438/419 |
| 2018/0243018 | A1 | 8/2018 | Lintula et al. |

OTHER PUBLICATIONS

International Search Report and Written Opinion of the International Searching Authority for PCT/US2018/018821, dated Jun. 22, 2018, 18 pages.

* cited by examiner

BONE IMPLANT DEVICES, INSTRUMENTS AND METHODS OF USE

CROSS-REFERENCE TO RELATED APPLICATION

This application is a continuation of PCT Application No. PCT/US2018/022079 filed on Mar. 12, 2018, which claims priority benefit under 35 U.S.C. § 119(e) of U.S. provisional application No. 62/469,748, filed Mar. 10, 2017, which is incorporated herein by reference in its entirety.

TECHNICAL FIELD

This invention relates generally to a bone implant device, and more particularly, to a bone implant for fusing adjacent phalanges in a foot or hand.

BACKGROUND OF THE INVENTION

Many disorders can affect toe or finger joints, causing pain and preventing the foot or hand from functioning as they should. These problems may be inherited from abnormally long toes, flat feet or high arches, or acquired from wearing poor fitting footwear or a fractured toe, which can further aggravate the deformities and cause more pain. Toe deformities in, for example, adults result mainly from an imbalance of the tendons, causing them to stretch or tighten abnormally. Arthritis is another major cause of discomfort and deformity in fingers and toes. The most common digital deformities in the foot are hammertoes, claw toes and overlapping and underlapping toes.

Podiatrists and orthopedists commonly use surgical procedures to alleviate the discomfort of, for example, a hammertoe and other abnormalities of the toe and finger joints and to prevent recurrence of the deformity. In the case of a hammertoe, surgeons may perform a proximal interphalangeal joint ("PIPJ") arthrodesis with the use of, for example, a Kirschner wire ("K-wire"), or insert a prosthetic device into adjoining phalanges of the toe, which serve to function as a normal knuckle or joint would. In the past, a surgeon used a threaded and/or ribbed/barbed implant made from a metallic or thermoplastic material, which are not biocompatible and have issues with osseointegration.

SUMMARY OF THE INVENTION

The shortcomings of the prior art may be alleviated by using a bone implant for fusing adjacent phalanges constructed in accordance with one or more principles or aspects of the present invention. The bone implant may be used in a variety of surgical procedures, including, for example, repairing hammertoes. Additionally, other uses of the bone implant constructed in accordance with different aspects of the present invention may be contemplated that fall within the scope of the claimed invention but which are not specifically described below.

In one aspect of the invention, there is provided a device to facilitate fusion between two adjacent phalanges in a body. The device comprises an elongated cylindrical member. The elongated cylindrical member includes a first end, a second end and an outer surface extending between the first end and the second end. A first circumferential recess is formed in the outer surface proximate the first end and a second circumferential recess is formed in the outer surface proximate the second end. The device also includes a first band of plasma sprayed material disposed within the first circumferential recess and protruding radially outward beyond the outer surface of the elongated cylindrical member, and a second band of plasma sprayed material disposed within the second circumferential recess and protruding radially outward beyond the outer surface of the elongated cylindrical member.

In another aspect of the invention, the bone implant device may be bent at an anatomically appropriate angle between the first band of plasma sprayed material and the second band of plasma sprayed material.

In another aspect of the invention, the first band of plasma sprayed material and the second band of plasma sprayed material both extend radially beyond the outer surface of the elongated member by approximately 0.060 mm.

In another aspect of the invention, a method for inserting a bone implant device including first and second bands of plasma sprayed material into a first phalange and a second adjacent phalange so as to fuse the first phalange to the second phalange and a method for an operative procedure for fusing a first phalange to a second adjacent phalange with a bone implant device including first and second bands of plasma sprayed material are described herein.

Additional features and benefits will become apparent from the following drawings and descriptions of the invention. Other embodiments and aspects of the invention are described in detail herein and are considered a part of the claimed invention.

BRIEF DESCRIPTION OF THE DRAWINGS

The subject matter which is regarded as the invention is particularly pointed out and distinctly claimed in the claims at the end of the specification. The foregoing and other objects, features, and advantages of the invention are apparent from the following detailed description taken in conjunction with the accompanying drawings in which:

DETAILED DESCRIPTION

Figure 1:
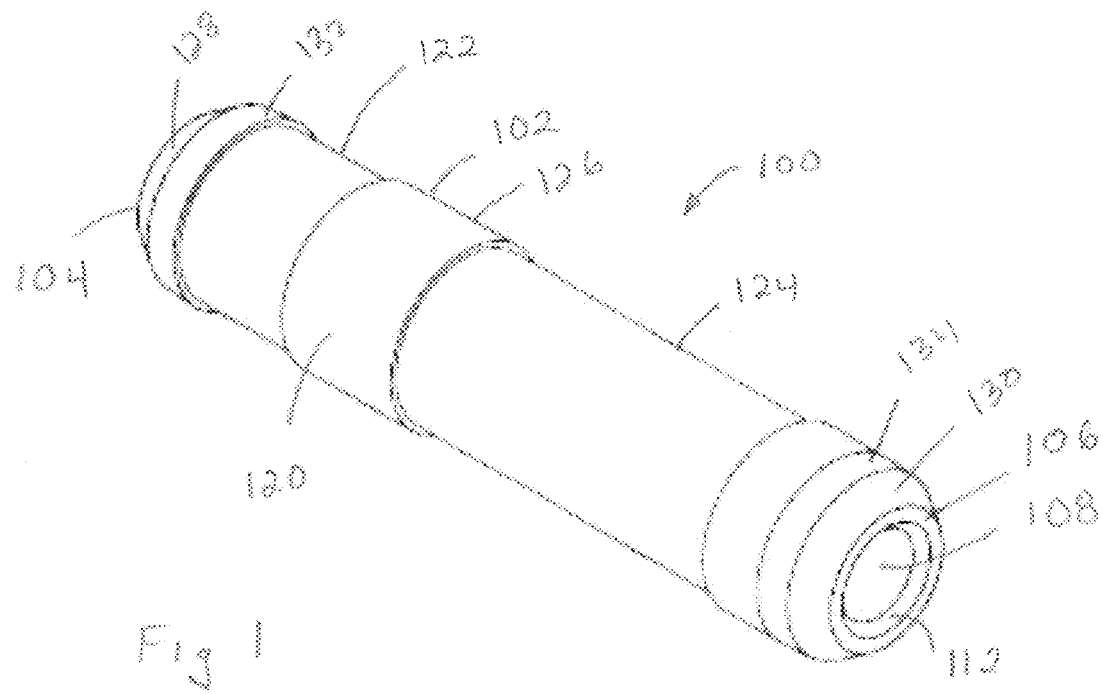
FIG. 1 depicts a perspective view of one embodiment of a bone implant constructed in accordance with one or more aspects of the present disclosure.

For the purposes of promoting an understanding of the principles of a bone implant designed and constructed in accordance with one or more aspects of the present disclosure, reference will now be made to the embodiments, or examples, illustrated in the drawings and specific language will be used to describe these. It will nevertheless be understood that no limitation of the scope of the disclosure is thereby intended. Any alterations and further modifications in the described embodiments, and any further applications of the principles or aspects of the disclosure as described herein are contemplated as would normally occur to one skilled in the art to which the bone implant device relates.

In this detailed description and the following claims, the words proximal, distal, anterior or plantar, posterior or dorsal, medial, lateral, superior and inferior are defined by their standard usage for indicating a particular part or portion of a bone or implant according to the relative disposition of the natural bone or directional terms of reference. For example, "proximal" means the portion of a device or implant nearest the torso, while "distal" indicates the portion of the device or implant farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure. Further, specifically in regards to the foot, the term "dorsal" refers to the top of the foot and the term "plantar" refers the bottom of the foot.

Similarly, positions or directions may be used herein with reference to anatomical structures or surfaces. For example, as the current implants, devices, instrumentation and methods are described herein with reference to use with the bones of the foot, the bones of the foot, ankle and lower leg may be used to describe the surfaces, positions, directions or orientations of the implants, devices, instrumentation and methods. Further, the implants, devices, instrumentation and methods, and the aspects, components, features and the like thereof, disclosed herein are described with respect to one side of the body for brevity purposes. However, as the human body is relatively symmetrical or mirrored about a line of symmetry (midline), it is hereby expressly contemplated that the implants, devices, instrumentation and methods, and the aspects, components, features and the like thereof, described and/or illustrated herein may be changed, varied, modified, reconfigured or otherwise altered for use or association with another side of the body for a same or similar purpose without departing from the spirit and scope of the invention. For example, the implants, devices, instrumentation and methods, and the aspects, components, features and the like thereof, described herein with respect to the right foot may be mirrored so that they likewise function with the left foot. Further, the implants, devices, instrumentation and methods, and the aspects, components, features and the like thereof, disclosed herein are described with respect to the foot for brevity purposes, but it should be understood that the implants, devices, instrumentation and methods may be used with other bones of the body having similar structures.

Presented herein is a bone implant designed to fuse adjacent phalanges in a patient's hand or foot. In one example, a bone implant constructed in accordance with one or more aspects of the present disclosure may be used during a hammertoe surgical procedure to assist in fusing the ends of adjacent phalange. The bone implant may be used to keep the toe straight or at an anatomical angle while the bone ends fuse together. The bone implant may be a cylindrical hollow tube and member that includes an elongated opening, cannulation or canal to receive, for example, a K-wire or a trocar. In an alternative embodiment, bone implant may be a solid rod, without any opening therethrough. Although the examples herein may be directed to a bone implant used to correct a hammertoe deformity, it is understand that a bone implant constructed in accordance with one or more aspects of the present invention may be used to correct other deformities in the foot or deformities in a hand.

Figure 2:
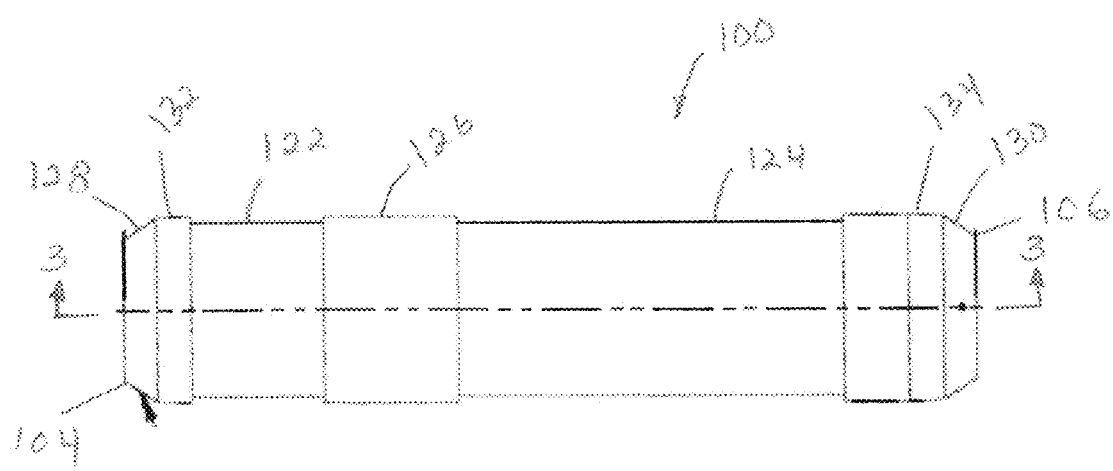
FIG. 2 depicts a side view of the bone implant of FIG. 1, in accordance with an aspect of the present disclosure.
Figure 3:
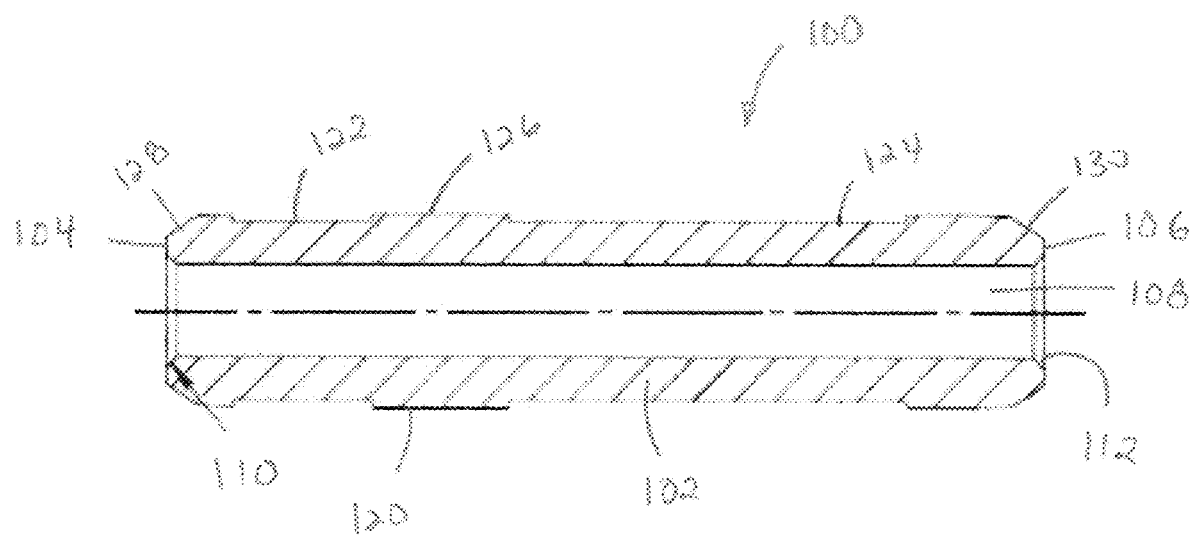
FIG. 3 depicts a cross-sectional view the bone implant depicted in FIG. 2 taken along the line 3-3, in accordance with an aspect of the present disclosure.

FIGS. 1-3 illustrate one example of a bone implant or implant 100 constructed in accordance with one or more aspects of the present invention. The bone implant 100 includes an elongated cylindrical tube, elongated cylindrical member, or body portion 102 including a first end 104 and a second end 106. In one example, the tube 102 may be, for example, approximately 14 mm long. In alternative embodiments, the tube 102 may be, for example, 16 mm long. However, the tube 102 may be made of any length for the desired specific application. The tube 102 defines an inner elongated opening or canal 108 extending from first end 104 to second end 106. In one example, the inner elongated opening 108 may be sized to be compatible with or receive standard K-wires that are traditionally used for hammertoe surgical procedures. In another embodiment, the inner elongated opening 108 may have a diameter of, for example, 1.5 mm+/−0.05 mm. In an alternative embodiment, the inner elongated opening 108 may have a diameter of, for example, 1.7 mm+/−0.05 mm. However, the elongated opening 108 may be formed with any diameter for the desired specific application.

As illustrated in FIG. 3, the elongated opening 108 may include an internal taper or angled internal edge 110, 112 extending radially inward from first and second ends 104, 106 to allow bone implant 100 to pass over a K-wire easily.

In one example, the inner taper 110, 112 may taper at an angle of, for example, forty-five degrees relative to a longitudinal axis extending through the center of the elongated opening 108. The tube 102 may be made from, for example, polyether ether ketone (PEEK) or a like material as known by one of ordinary skill in the art.

The bone implant 100 includes an outer surface 120 extending between first end 104 and second end 106. In one example, outer surface 120 includes a first circumferential groove or recess 122 spaced from first end 104 and a second circumferential groove or recess 124 spaced from second end 106. The first and second circumferential recesses 122, 124 are separated by an intermediate portion or region 126. In one embodiment, the first circumferential recess 122 is space, for example, approximately 1.25 mm from first end 104, the second circumferential recess 124 is spaced, for example, approximately 2.5 mm from second end 106, and the intermediate region 126 is, for example, 2.5 mm. However, these dimensions may be varied depending on the desired specific application.

In one embodiment, the outer surface 110 includes a first chamfered, angled or sloping surface 128 between the first recess 122 and the first end 104 that slants radially inward towards the first end 104 and a second chamfered, angled or sloping surface 130 between the second recess 124 and the second end 105 that slants radially inward towards second end 106. The first and second angled surfaces 128, 130 allow for easy and immediate insertion of the phalanx over the first and second ends 104, 106. The first and second angled surfaces 128, 130 may also provide, for example, a lead-in ramp at the first and second ends 104, 106 to properly strain the phalanx bone in anticipation for optimal insertion and bedding of the bone implant 100 and osteo-synthesis interference with the cancellous bone. In one example, the first and second angled surfaces 128, 130 may slope, for example, approximately thirty degrees relative to a longitudinal axis extending through the center of the elongated opening 108.

The outer surface 120 may also include a third angled surface 132 extending from the first angled surface 128 to the first circumferential recess 122 and a fourth angled surface 134 extending from the second angled surface 130 towards the second circumferential recess 124. The third and fourth angled surfaces 132, 134 may include, for example, a milder angle or slope as compared to the first and second angled surfaces 128, 130. In one example, the third and fourth angled surfaces 132, 134 may slope, for example, approximately three degrees relative to a longitudinal axis extending through the center of the elongated opening 108.

Figure 4:
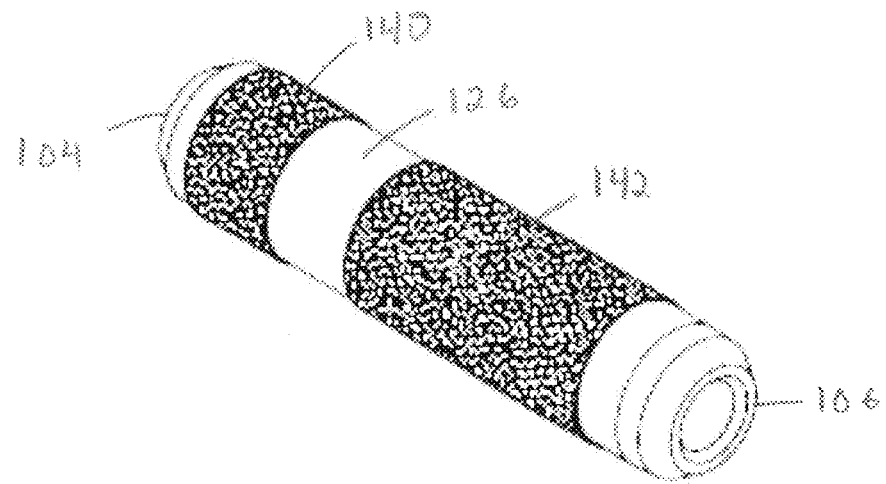
FIG. 4 depicts a perspective view of one embodiment of a bone implant constructed in accordance with one or more aspects of the present disclosure.

As illustrated in an embodiment depicted in FIG. 4, the first circumferential recess 122 is sized to receive a first band of titanium plasma spray 140 and second circumferential recess 124 is sized to receive a second band of titanium plasma spray 142. In one embodiment, the tube 102 may be approximately 14 mm long, the first circumferential recess 122 is 2.5 mm wide, and the second circumferential recess 124 is 5.25 mm wide. In another embodiment, the tube 102 may be approximately 16 mm long, the first circumferential recess 122 is 2.5 mm wide, and the second circumferential recess 124 is 7.25 mm wide. However, the length of the first and second circumferential recesses 122, 124 may be adjusted depending on the specific desired application.

The use of a titanium plasma spray encourages both in-growth and on-growth of bone. For example, titanium plasma spray provides osteoconductive properties to serve as a scaffold for viable bone healing by allowing bone ingrowth into the tube 102 to provide increased stability for long term success of the bone implant 100. Titanium plasma spray also provides osteoinductive properties to encourage on bone growth enhancement. One example of a titanium plasma spray that can be used with the bone implant 100 is commercially available from Surface Dynamics of Cincinnati, Ohio. The first and second bands of titanium plasma spray 140, 142 within the first and second circumferential recess 122, 124 produces a continuous self-supporting ring that does not delaminate from the cylindrical bone implant 100, which is a common problem when a titanium plasma spray is used on planar surfaces of PEEK implants.

Figure 7:
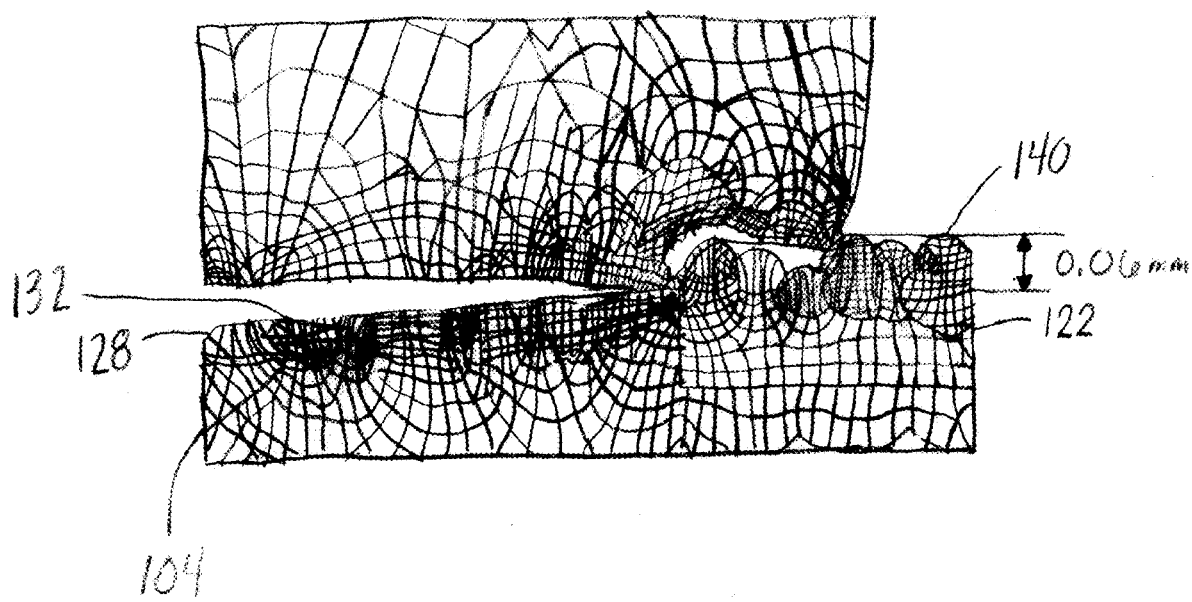
FIG. 7 depicts a partial sectional view of one embodiment of a bone implant constructed in accordance with one or more aspects of the present disclosure seated within cancellous bone.

Titanium plasma spray technology typically sprays a thick layer having, for example, a thickness of 0.190 mm. The first and second circumferential recesses 122, 124 allow for at least a portion of this thickness to be recessed below the outer surface 120 and for a desired portion of the first and second bands of titanium plasma spray 140, 142 to protrude or extend radially beyond the outer surface 120. With the first and second circumferential recesses 122, 124, a minimum prominence beyond the outer surface 120, as illustrated in FIG. 7, is established by undercutting the outer surface 120 to inset the titanium plasma spray within the first and second circumferential recesses 122, 124. The minimum prominence beyond the outer surface 120 of the first and second bands of titanium plasma spray 140, 142 allows for elastic deformation of the bone instead of broaching during insertion. The length of the first and second bands 140, 142 are maximized to allow osseointegration while still allowing for implant removal, if necessary. In one embodiment, there is more titanium plasma spray proximally (e.g. within the second circumferential recess 124) than distally (e.g. within the first circumferential recess 122) to prevent the bone implant 100 from moving while inserting the bone implant 100 into the middle phalanx. For example, the second band 142 may be at least 25% longer than the first band 140. In another example, the second band 142 may be 110% longer than the first band 140.

A bone implant 100 constructed in accordance with one or more aspects of the present disclosure is designed to ensure an optimal press fit interference into the bone for better healing. In one example, the depth of the first and second circumferential recesses 122, 124 allows for the first and second bands 140, 142 to extend, for example, approximately 0.060 mm beyond or radially outward from the outer surface 120 to foster optimal healing environment between the bone implant 100 and the cancellous bone. A 0.060 mm prominence of titanium plasma spray extending radially beyond the outer surface 120 allows for elastic deformation of the bone instead of broaching during insertion of the bone implant 100. With a 0.060 mm prominence, the depth of the first and second circumferential recesses 122, 124 may be, for example, 0.13 mm since the typical thickness of titanium plasma spray is 0.190 mm. However, the depth of the first and second circumferential recesses 122, 124 may be adjusted depending on the thickness of the titanium plasma spray to result in a 0.060 mm prominence beyond the outer surface 120.

The length of the first band of titanium plasma spray 140 is optimally sized to ensure easy insertion within a phalanx while maximizing osteointegration of the titanium plasma spray. The length of the second band of titanium plasma spray 142 is optimally sized for insertion into and grip within, for example, a proximal phalanx. In one embodiment, the longer length of the second band 142 as compared to the first band 140 allows for additional room for the titanium plasma spray and fixation with the phalanx. The first and second bands 14, 142 may also be sized to match the relative bone lengths.

Figure 5:
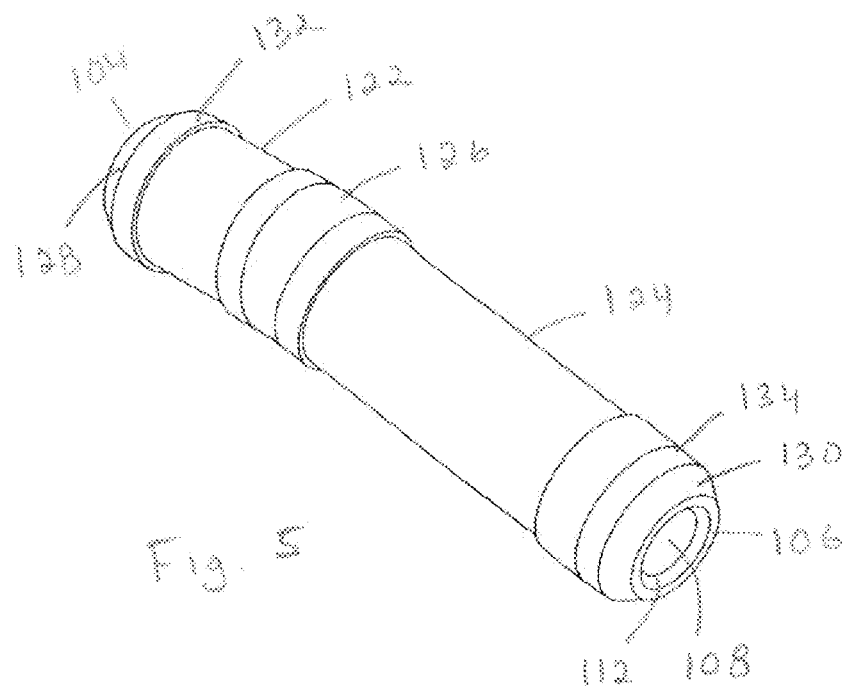
FIG. 5 depicts a perspective view of another embodiment of a bone implant including an anatomical angle constructed in accordance with one or more aspects of the present disclosure.
Figure 6:
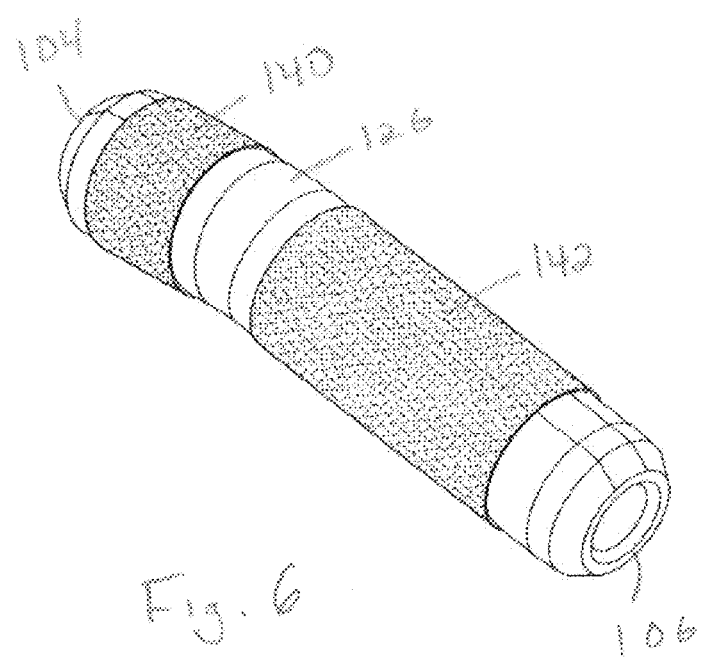
FIG. 6 depicts a perspective view of another embodiment of a bone implant including an anatomical angle constructed in accordance with one or more aspects of the present disclosure.

In one embodiment, the bone implant 100 may be a straight cylindrical tube, as illustrated in FIGS. 1-3. In an alternative embodiment illustrated in FIGS. 5-6, the bone implant 100 may be shaped to include an anatomically acceptable angle bent in the region of the intermediate portion 126. An angle of, for example, 0 to 10 degrees, normally exists between a proximal phalange and an intermediate phalange in healthy individuals to place the toe in a correct and anatomic position. An anatomically acceptable angle can be formed at or near the intermediate portion 126 so that the first end 104 and the second end 106 are slightly drawn towards one another. The specific size (e.g. length) and diameter of the bone implant 100 may be selected by a surgeon depending on, for example, the size of K-wire to be used or the bone in which the implant will be inserted. A bone implant 100 having a smaller diameter of, for example, 2.5 mm to 3.75 mm, may use a titanium plasma spray that matches the cancellous porous structure and create a ratcheting or interdigitating fit of the bone implant 100 into the cancellous structure.

The intermediate portion 126 of the outer surface 120 positioned between the first and second bands 140, 142 allows for the bone implant 100 to be cut without generating titanium debris from the plasma spray, should the bone implant 100 need to be removed after insertion. The intermediate portion 126 may also be optimally sized to allow variation in positioning of the bone implant 100 at the joint between adjacent phalanges. In one embodiment, the third and fourth angled surfaces 132, 134 of the outer surface 120 may include a milder angle or slope as compared to the first and second angled surfaces 128, 130 to allow the bone implant 100 to be easily inserted up to the first and second bands of titanium plasma spray 140, 142.

A bone implant constructed in accordance with one or more aspects of the present disclosure is useful in the orthopedic and podiatric fields to, for example, support versatility in surgical technique, allowing for surgeon preference to dictate technique. For example, a standard technique may be performed that allows direct drilling and placement of the implant. Also, a retrograde technique may be performed with initial K-wire placement to determine toe position. The retrograde technique allows for a K-wire to be left in to temporarily stabilize the MTP joint when used with, for example, a straight implant, if desired.

Figure 8:
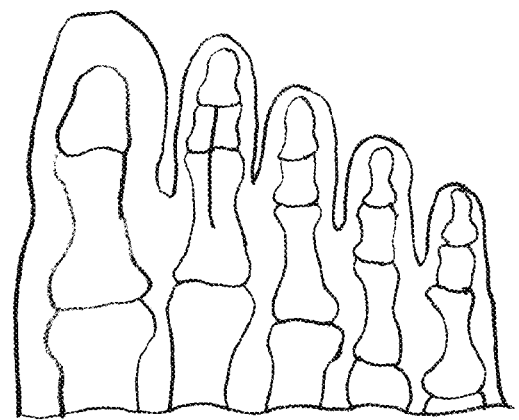
FIG. 8 depicts a partial sectional view of a human foot about to undergo a PIPJ arthrodesis procedure, in accordance with one embodiment of the present disclosure.

One example of a standard technique surgical procedure for inserting a bone implant 100 constructed in accordance with one or more aspects of the present disclosure is PIPJ arthrodesis, as illustrated in FIGS. 8-19. During this procedure, a podiatric or orthopedic surgeon would make a longitudinal or transverse incision, as shown in FIG. 8, followed by dissection down to expose the proximal interphalangeal joint.

Figure 9:
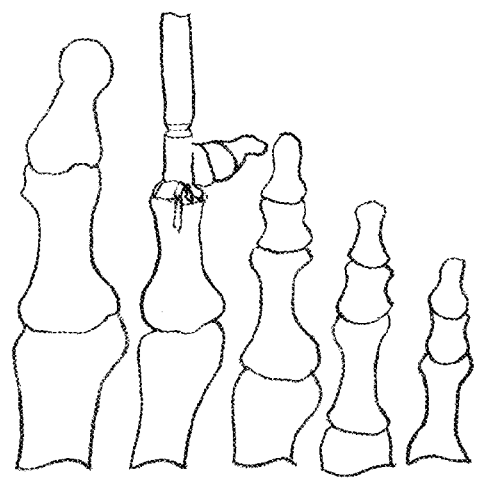
FIG. 9 depicts a partial sectional view of a human foot that is undergoing a PIPJ arthrodesis procedure, in accordance with one embodiment of the present disclosure.
Figure 10:
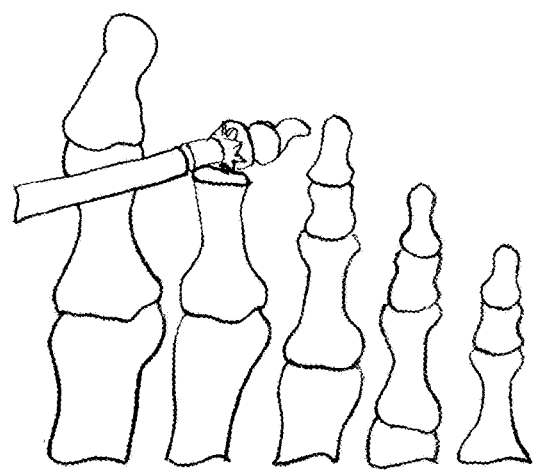
FIG. 10 depicts a partial sectional view of a human foot that is undergoing a PIPJ arthrodesis procedure, in accordance with one embodiment of the present disclosure.

The joint between the proximal phalanx and intermediate phalanx is then prepared by the surgeon. A sagittal saw may be used to resect the cartilage at the head of the proximal phalanx. It may be necessary to make the cut at the level of the condyles to allow passage of the implant into the middle phalanx during insertion. A planer can be used to remove cartilage form the proximal phalanx or to provide further resection after the sagittal saw cut. A trocar insert may then be placed inside the planer. As illustrated in FIG. 9, the trocar is then centered on the proximal phalanx. The planer should begin to move prior to contacting the bone. The planer should continue to engage until all the cartilage is removed from the head of the proximal phalanx. As illustrated in FIG. 10, the planer is then used for cartilage resection on the middle phalanx bone. The trocar should be centered on the middle phalanx and movement of the planer should occur prior to contacting the bone. The planer should continue to engage until no cartilage remains.

Figure 11:
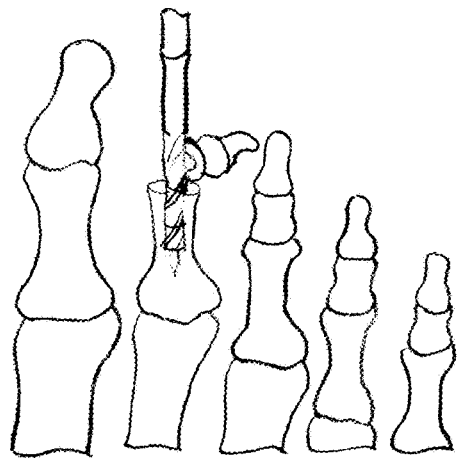
FIG. 11 depicts a partial sectional view of a human foot that is undergoing a PIPJ arthrodesis procedure, in accordance with one embodiment of the present disclosure.
Figure 12:
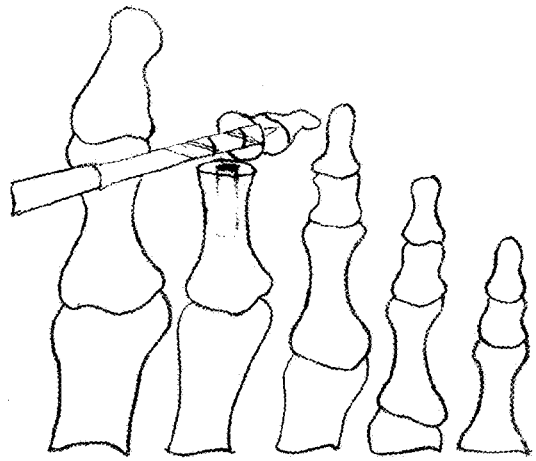
FIG. 12 depicts a partial sectional view of a human foot that is undergoing a PIPJ arthrodesis procedure, in accordance with one embodiment of the present disclosure.

Next, the bones are prepared to accept or receive the bone implant 100. A surgical tool, such as, for example, a surgical trocar and drill, may be used to create bores or holes in the end surfaces of the proximal and the intermediate phalanges for insertion of the bone implant 100. In one example, the trocar/drill is centered on the proximal phalanx and used to drill down to a desired depth, as depicted in FIG. 11. The same trocar/drill unit may then be used to drill the middle phalanx by centering the trocar on the middle phalanx and drilling down to a desired depth, as illustrated in FIG. 12.

Figure 13:
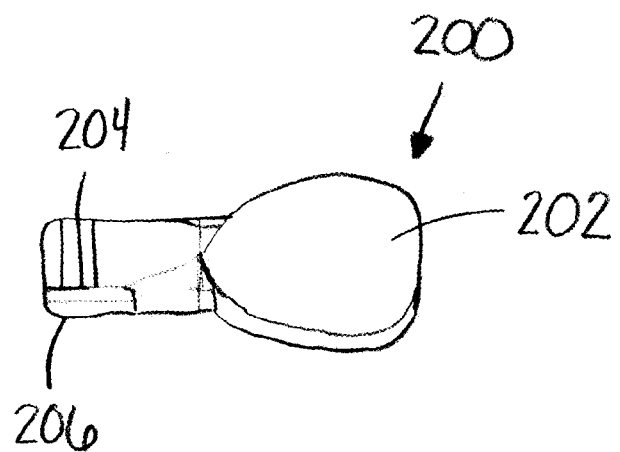
FIG. 13 depicts a perspective view of one embodiment of an inserter that may be used during a PIPJ arthrodesis procedure to insert a bone implant constructed in accordance with one or more aspects of the present disclosure into a bore formed in a phalange bone.
Figure 14:
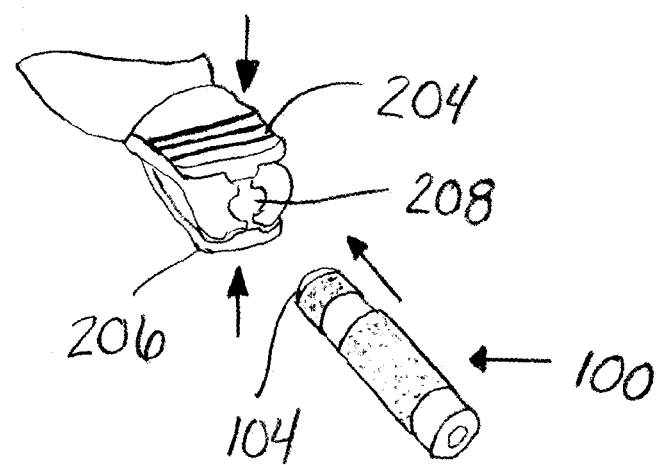
FIG. 14 depicts a perspective view of one way to load the inserter illustrated in FIG. 13 with a bone implant constructed in accordance with one or more aspects of the present disclosure.
Figure 15:
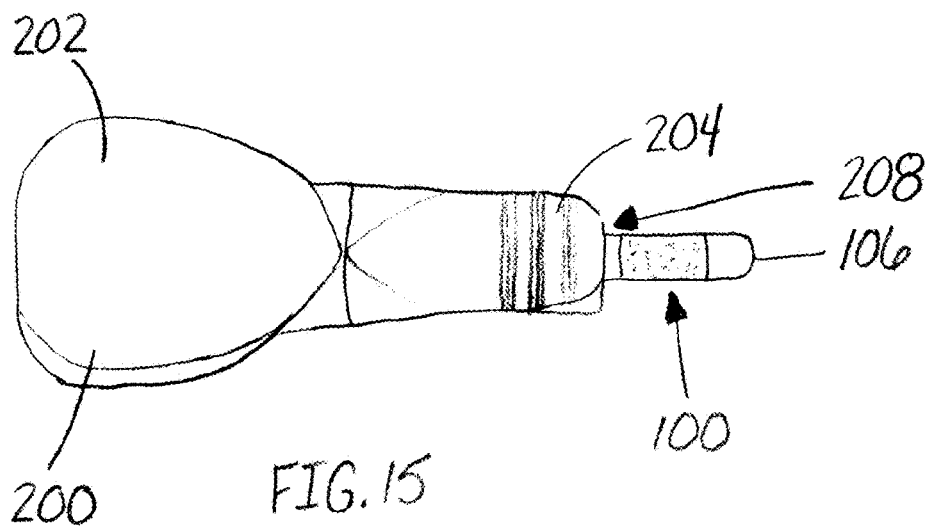
FIG. 15 depicts a perspective view of the inserter illustrated in FIG. 13 with a bone implant loaded therein and constructed in accordance with one or more aspects of the present disclosure.

Once the bores are drilled, a suitable bone implant 100 with the desired anatomical angle is selected and inserted. In one example, an inserter 200, as illustrated in FIG. 13-15, may be used to assist in inserting the bone implant 100. For example, the inserter 200 may include a thumb segment 202 and two movable tabs 204, 206. During loading of the bone implant 100 into the inserter 200, a surgeon depresses the movable tabs 204, 206 to open up a space 208 for receiving or accepting the first end 104 of the bone implant 100. A portion of the bone implant 100 is inserted into the space 208 up to the desired portion to be inserted into the proximal phalanx. When the movable tabs 204, 206 are released, the space 208 closes and the movable tabs 204, 206 secure the bone implant 100 against the outer surface 120 and a portion of the first band 124. In this example, the second band 126 is fully seated into the bone and stops the bone implant 100 at the joint where there is not titanium plasma spray.

Figure 16:
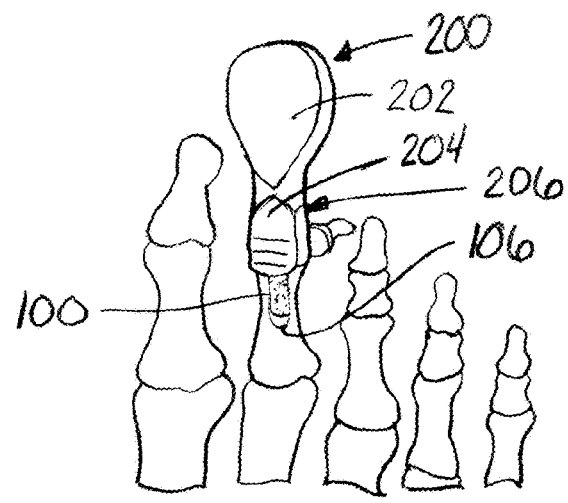
FIG. 16 depicts a partial sectional view of a human foot that is undergoing a PIPJ arthrodesis procedure, in accordance with one embodiment of the present disclosure.
Figure 17:
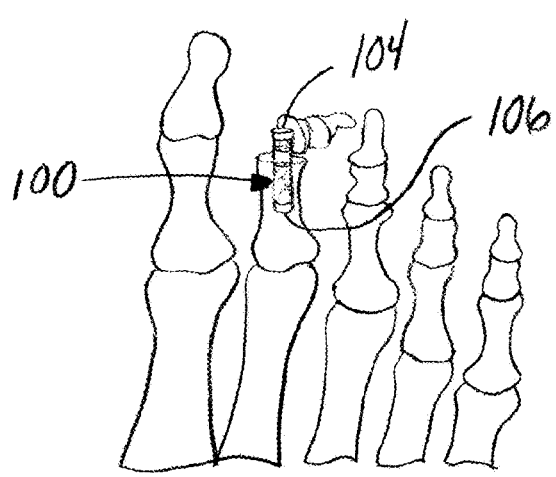
FIG. 17 depicts a partial sectional view of a human foot that is undergoing a PIPJ arthrodesis procedure, in accordance with one embodiment of the present disclosure.
Figure 18:
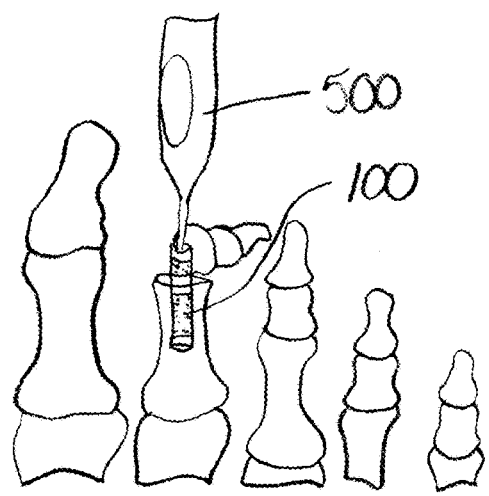
FIG. 18 depicts a partial sectional view of a human foot that is undergoing a PIPJ arthrodesis procedure, in accordance with one embodiment of the present disclosure.

After the bone implant 100 is loaded into the inserter 200 (see FIG. 15), the second end 106 of the bone implant 100 is inserted into the proximal phalanx drill hole or bore, as shown in FIG. 16. When the bone implant 100 is fully seated, the inserter 200 will be contacting the distal surface of the proximal phalanx, and no further advancement can be achieved. The surgeon then depresses the movable tabs 204, 206 of the inserter 200 to release the bone implant 100 into its seated position within the hole or bore of the proximal phalanx, as illustrated in FIG. 17.

Figure 19:
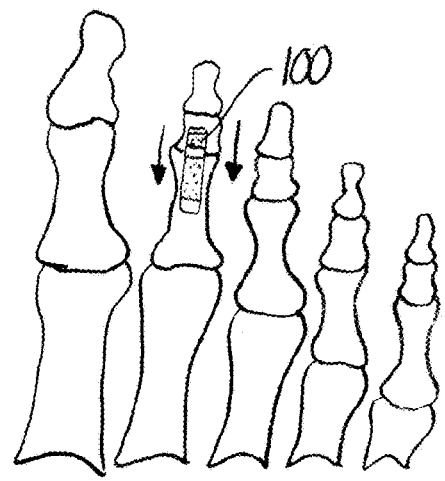
FIG. 19 depicts a partial sectional view of a human foot that is undergoing a PIPJ arthrodesis procedure, in accordance with one embodiment of the present disclosure.

The remaining portion of the bone implant 100 is oriented in an anatomically correct position with respect to the middle phalanx. The distal portion of the toe is then pulled distally and dorsally to allow the protruding first end 104 and the distal portion of the bone implant 100 to seat within the drilled hole or bore in the middle phalanx. If, for example, the middle phalanx is unable to be pulled over the bone implant 100, increased soft tissue release can be performed at the PIPJ. If the implant still cannot be placed in the middle phalanx, a surgeon can use an implant puller 500, as illustrated, for example, in FIG. 18, to remove the bone implant 100 and use the planer to remove more bone at the PIPJ. The implant puller 500 can also be used if bone implant 100 re-positioning is required without causing damage to the first and second bands of titanium plasma spray 124, 126. Once seated, pressure may be applied proximally to the distal aspect of the toe until apposition of the proximal and middle phalanges is achieved, as illustrated in FIG. 19.

Figure 20:
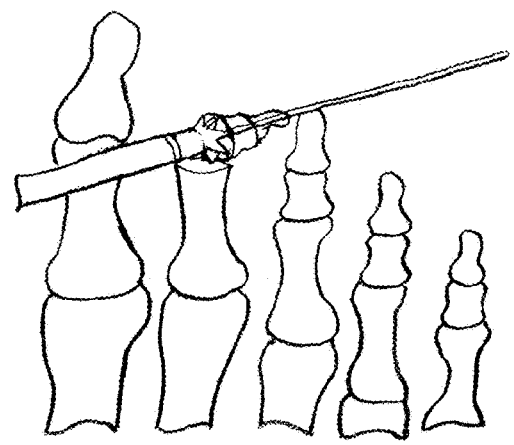
FIG. 20 depicts a partial sectional view of a human foot that is undergoing a PIPJ arthrodesis procedure, in accordance with one embodiment of the present disclosure.
Figure 21:
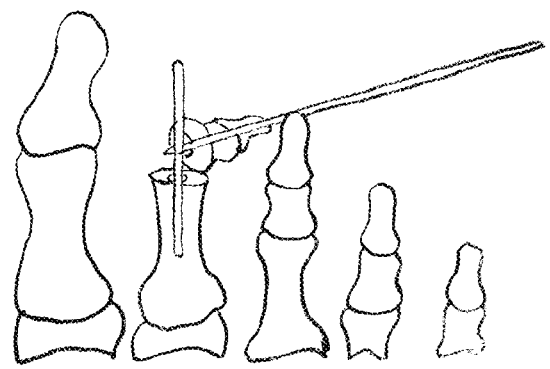
FIG. 21 depicts a partial sectional view of a human foot that is undergoing a PIPJ arthrodesis procedure, in accordance with one embodiment of the present disclosure.
Figure 22:
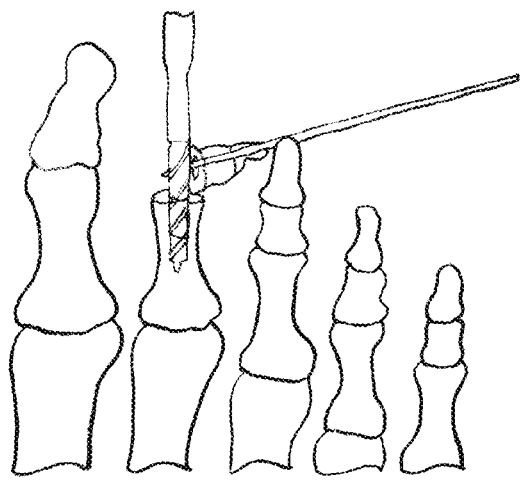
FIG. 22 depicts a partial sectional view of a human foot that is undergoing a PIPJ arthrodesis procedure, in accordance with one embodiment of the present disclosure.
Figure 23:
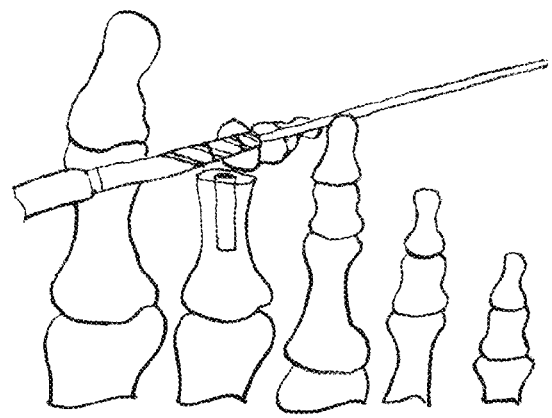
FIG. 23 depicts a partial sectional view of a human foot that is undergoing a PIPJ arthrodesis procedure, in accordance with one embodiment of the present disclosure.
Figure 24:
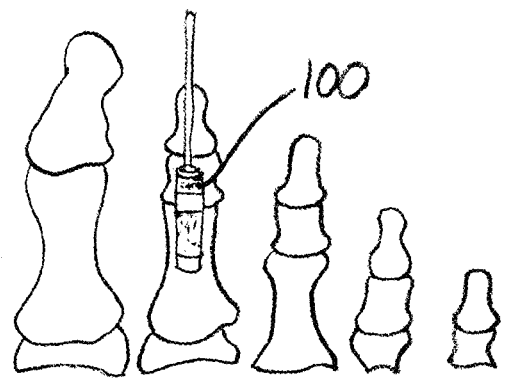
FIG. 24 depicts a partial sectional view of a human foot that is undergoing a PIPJ arthrodesis procedure, in accordance with one embodiment of the present disclosure.
Figure 25:
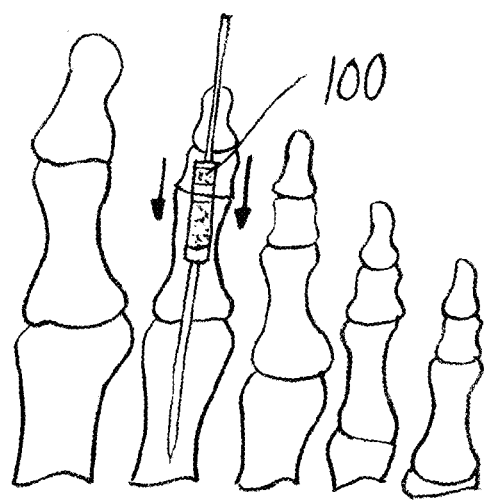
FIG. 25 depicts a partial sectional view of a human foot that is undergoing a PIPJ arthrodesis procedure, in accordance with one embodiment of the present disclosure.

During a retrograde technique surgical procedure using a bone implant 100 constructed in accordance with one or more aspects of the present invention, a K-wire is positioned centrally on the proximal phalanx with position confirmed via fluoroscopy. A planer is then slide over the K-wire. The planer should start moving prior to contacting the bone and continue until all cartilage is removed from the head of the proximal phalanx. The K-wire is then removed from the proximal phalanx when planing is complete. In preparing the middle phalanx, as illustrated in FIG. 20, the optimal position of the K-wire is determined and then the K-wire is pulled distally such that only 2-3 mm of wire protrudes from the base of the middle phalanx. The planer is placed over the K-wire extending from the middle phalanx. The planer should start moving prior to contacting the bone and continue until no cartilage remains. The proximal phalanx bone is then prepared by placing a blunt K-wire in the canal of the proximal phalanx (see e.g. FIG. 21) and drilling over the blunt K-wire to a desired depth (see e.g. FIG. 22). The blunt K-wire is then removed and the same drill may be used to drill the middle phalanx by inserting a K-wire into the cannula of the drill and drilling until a desired depth is achieved (see e.g. FIG. 23). At this time, an appropriate sized bone implant 100 may be selected and inserted, for example, using inserter 200 (as illustrated in FIGS. 13-15), first into the proximal phalanx drill hole and then the middle phalanx drill hole. The distal portion of the toe is then pulled distally and dorsally to allow the protruding distal portion of the bone implant 100 to seat within the drilled hole in the middle phalanx and the K-wire to sit within the cannulation of the bone implant 100 (see e.g. FIG. 24). Once the bone implant 100 is seated, pressure may be applied proximally to the distal aspect of the toe until apposition of the proximal and middle phalanges is achieved (see e.g. FIG. 25). A K-wire is then driven proximally into the proximal phalanx and into the metatarsal, if desired.

Figure 26:
FIG. 26 depicts a side view of one embodiment of an extractor that may be used to remove a bone implant constructed in accordance with one or more aspects of the present disclosure from a phalange.
Figure 27:
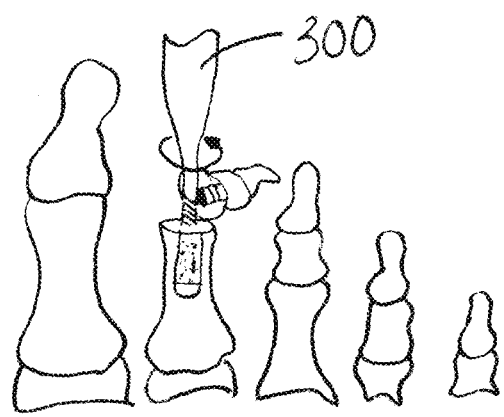
FIG. 27 depicts a partial sectional view of a human foot that is undergoing a procedure to remove a bone implant from a phalange constructed in accordance with one or more aspects of the present disclosure with the extractor depicted in FIG. 26, in accordance with one embodiment of the present disclosure.

Removal or revision of the bone implant 100 may be necessary by a surgeon. For bone implants 100 that are integrated into the bones of the phalanges and/or where bony fusion has occurred across the PIPJ, a surgeon may use, for example, an extractor 300, as depicted in FIG. 26. The bone implant 100 may be removed by, for example, first using a sagittal saw to cut through the joint and the bone implant 100 (preferably through intermediate portion 126). Once the canal or elongated opening 108 of bone implant is visible, the extractor 300 can be threaded into the canal side of the bone implant 100 by turning in, for example, a counter-clockwise direction (see e.g. FIG. 27). Once the extractor 300 is solidly inserted into one side of the bone implant 100, the surgeon can either continue counter-clockwise motion or rotation of the extractor 300 to force counter-clockwise rotation of the bone implant 100, thus loosening the bone implant 100 from the bone, or use a mallet to tap the base of the extractor 300 handle to loosen the bone implant 100 from the bone. This extraction process should be repeated on the second side of the bone implant 100 to complete removal of all portions of the bone implant 100.

Figure 28:
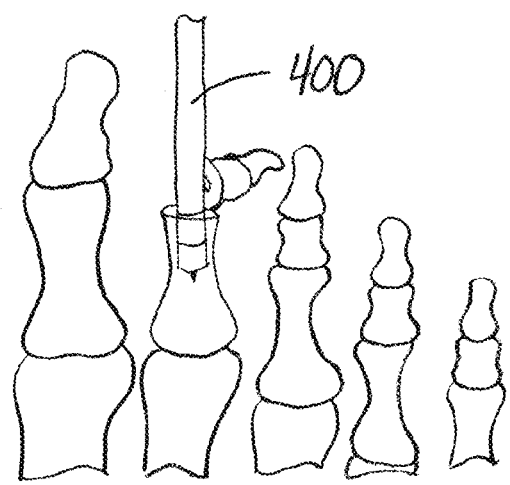
FIG. 28 depicts a partial sectional view of a human foot that is undergoing a procedure using a trephine, in accordance with one embodiment of the present disclosure.
Figure 29:
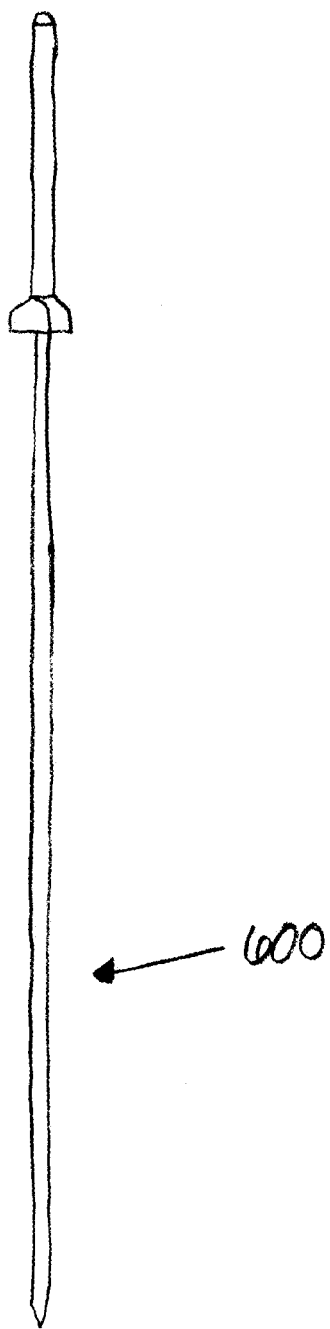
FIG. 29. depicts a side perspective view of a trocar in accordance with one or more aspects of the present disclosure.

If removal cannot be accomplished using the extractor 300, a trephine 400 may be used. A trephine 400 may be sized to the diameter of the bone implant 100 and is cannulated to allow for insertion of a trocar 600 (see FIG. 29) into the trephine 400. The tip of the trocar 600 is inserted into the elongated opening 108 of the bone implant 100 and the trephine 400 is inserted to a desired depth for removal of the portions of the bone implant 100 from the proximal phalanx and middle phalanx (see e.g. FIG. 28).

A bone implant 100 constructed in accordance with one or more aspects of the present disclosure may be designed to provide several advantages over a K-wire. For example, the bone implant 100 provides an ideal press fit between the bone implant 100 and the cancellous bone due to a controlled, precise interference between the drill hole and the titanium plasma spray. A PEEK bone implant 100 is biocompatible and closely matches the mechanical properties of bone. Also, the first and second bands of titanium plasma spray 140, 142 are located on strategic areas of the PEEK material to provide osteoconductive and osteoinductive properties, which allow for bone ingrowth into the bone implant 100 to provide increased stability over time. For example, a minimum length of PEEK, such as, for example, 1.25 mm, may be required distally to pull the toe or middle phalanx over the bone implant 100. Also, the instrumentation provides for ease of insertion or removal of the bone implant 100 from the bone.

A bone implant 100 constructed in accordance with one or more aspects of the present disclosure may provide more surgical options for untreated patients, may lessen the risk of implant placement within the forefoot, may provide a more biologically complaint design, and may provide surgeons future options while preserving bone stock.

Figure 30:
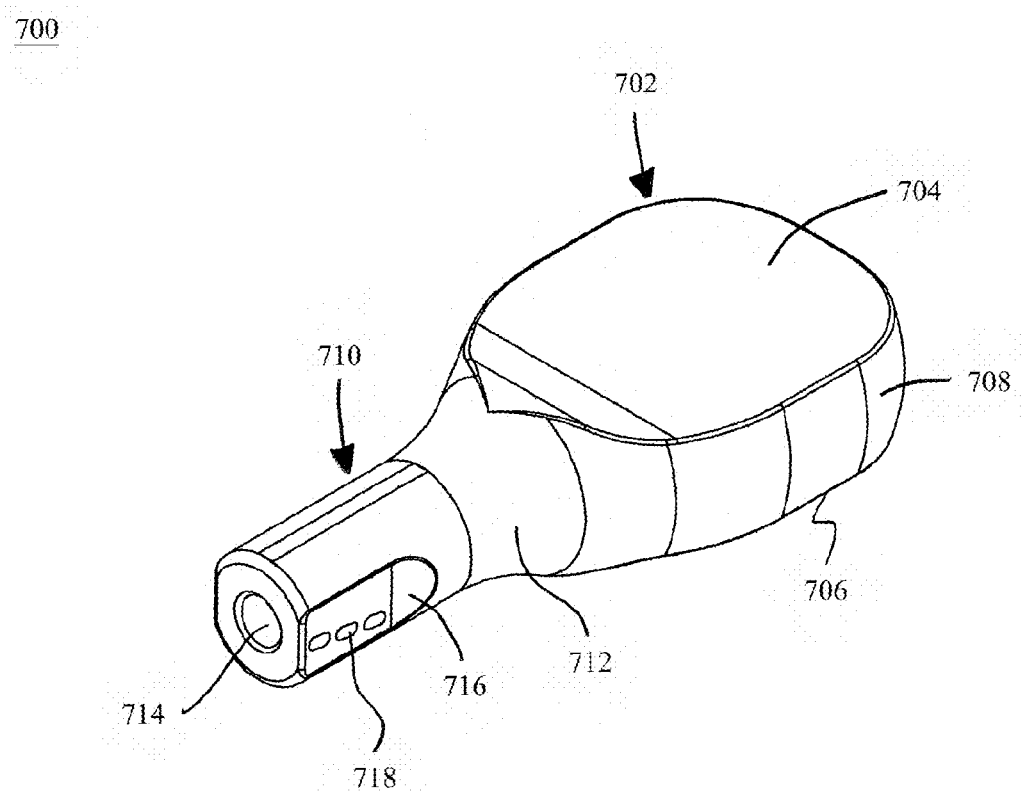
FIG. 30 is a first perspective view of an insertion instrument, in accordance with an aspect of the present invention.
Figure 31:
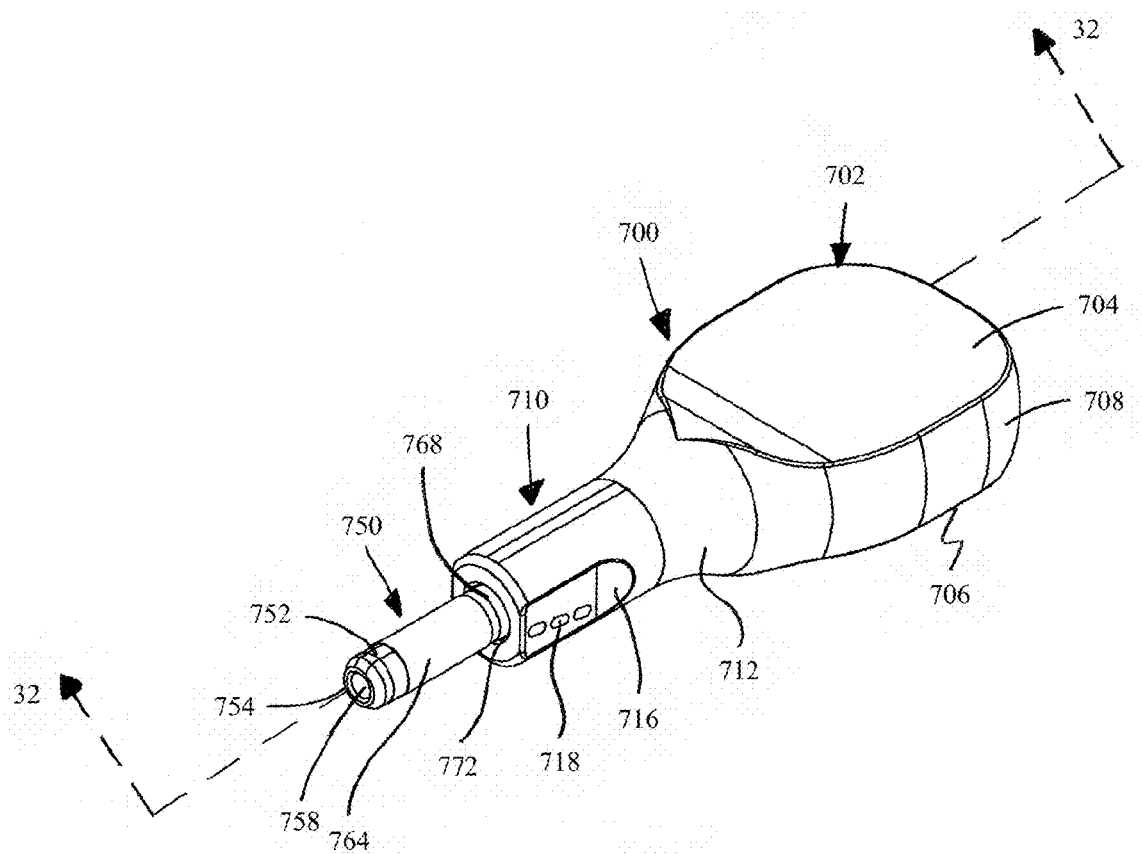
FIG. 31 is a perspective view of an implant inserted into the insertion instrument of FIG. 30, in accordance with an aspect of the present invention.
Figure 32:
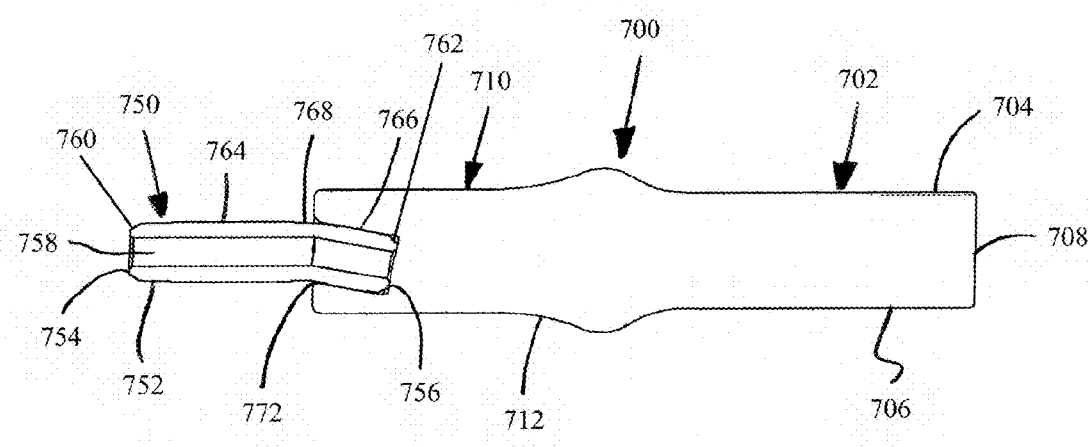
FIG. 32 is a cross-sectional view of the assembled implant and insertion instrument of FIG. 31 taken along line 32-32, in accordance with an aspect of the present invention.

Referring now to FIGS. 30-32, another insertion instrument 700 is shown. The insertion instrument 700 includes a body or handle portion 702 and a coupling member 710 extending away from a second end of the body or handle portion 702. The handle portion 702 may include a top surface 704, a bottom surface 706, and a side portion 708 extending between the top surface 704 and the bottom surface 706. The handle portion 702 may have a first width and the coupling member 710 may have a second width. The first width may be larger than the second width. The insertion instrument 700 may include a tapered portion 712 extending between the handle portion 702 and the coupling member 710. The coupling member 710 may include an opening 714 extending from a second end of the insertion instrument 700 into the coupling member 710 toward a first end of the insertion instrument 700. The coupling member 710 may also include, for example, planar sections 716 on the sides of the coupling member 710. The planar sections 716 may include alignment markings 718 showing the position or angulation of the opening 714. The angulation of the opening 714 may correspond to the position or angulation of the first protrusion 766 relative to the second protrusion 764, as shown in FIG. 32 to ensure implant 750 projects straight away from the insertion instrument 700.

Referring now to FIGS. 31 and 32, the implant 750 and corresponding insertion instrument 700 are shown. The insertion instrument 700 receives the implant 750 as shown in FIGS. 31 and 32. The implant 750 includes a body portion or elongated cylindrical tube or member 752 with a first end 754 and a second end 756. The implant 750 also includes an inner elongated opening or canal 758 extending through the body portion 752 from the first end 754 to the second end 756. The elongated opening 758 may also include internal tapers extending radially inward from the first and second ends 754, 756. The internal tapers of implant 750 may be of the type described above with reference to internal tapers 110, 112 of implant 100, which will not be described again here for brevity sake. The first end 754 may also include an exterior tapered or angled edge 760 and the second end 756 may include an exterior tapered or angled edge 762.

The implant 750 may also include a first protrusion or first band of plasma sprayed material 764 extending circumferentially away from the body portion 752 near the first end 754 of the implant 750. The plasma sprayed material in the first band 764 may be, for example, titanium or another biocompatible material as known by one of ordinary skill in the art. The first protrusion or band 764 may fill a first circumferential groove or recess (not shown). The first circumferential groove or recess (not shown) may be of the type described above with reference to the first circumferential groove or recess 122 of implant 100, which will not be described again here for brevity sake. The implant 750 may further include a second protrusion or second band of plasma sprayed material 766 extending circumferentially away from the body portion 752 near the second end 756 of the implant 750. The plasma sprayed material in the second band 766 may be, for example, titanium or another biocompatible material as known by one of ordinary skill in the art. The second protrusion or band 766 may fill a second circumferential groove or recess (not shown). The second circumferential groove or recess (not shown) may be of the type described above with reference to the second circumferential groove or recess 124 of implant 100, which will not be described again here for brevity sake. The first protrusion 764 may have a first length and the second protrusion 766 may have a second length. The first length may be, for example, longer than the second length. The first and second protrusions or bands of plasma sprayed material 764, 766 may form, for example, a textured surface allowing for bone on-growth. It is also contemplated that the first and second protrusions 764, 766 may have, for example, a smooth exterior surface. The body 752 may include a portion, central member, intermediate portion, or intermediate region 768 positioned between the first protrusion 764 and the second protrusion 766. As shown in FIGS. 31 and 32, the portion 768 of the body 752 is angled between the first and second protrusions 764, 766 to form an angled implant 750.

Figures 33, 34:
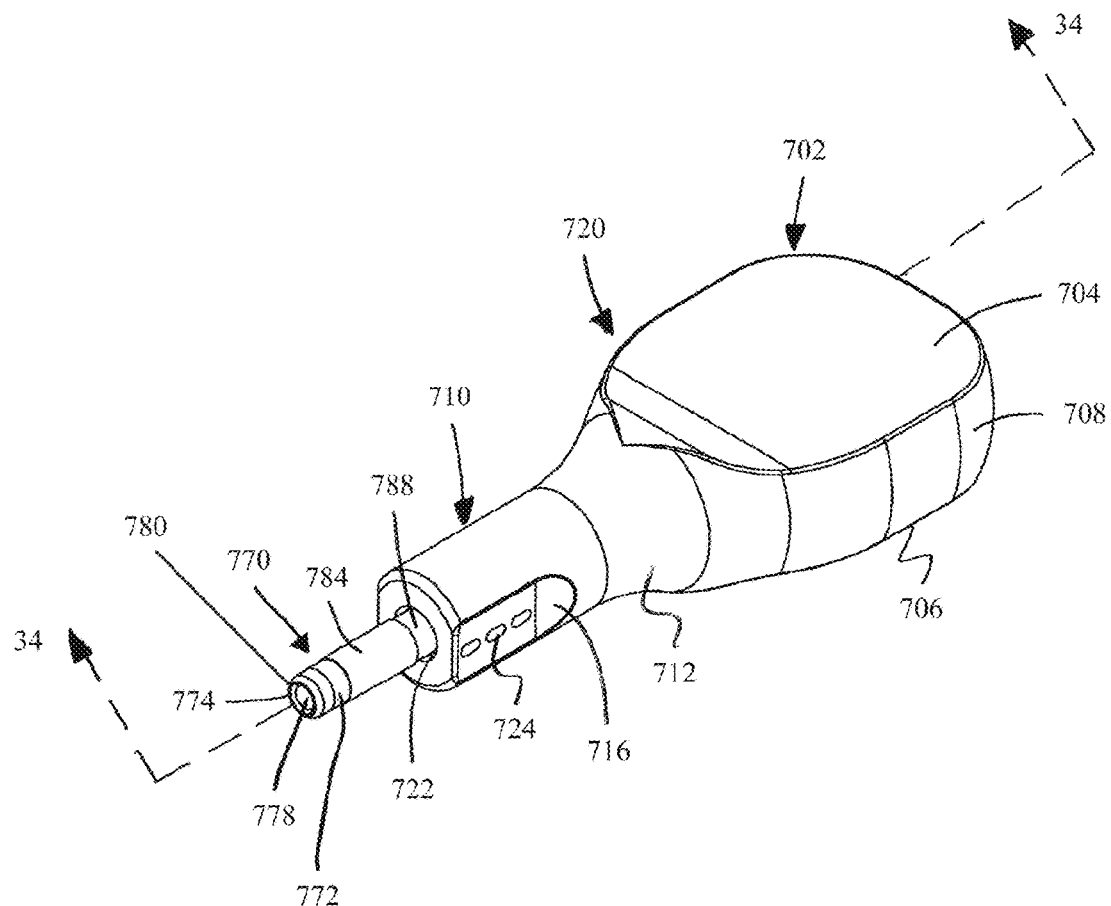
FIG. 33 is a perspective view of another implant inserted into another insertion instrument, in accordance with an aspect of the present invention.
FIG. 34 is a cross-sectional view of the assembled implant and insertion instrument of FIG. 33 taken along line 33-33, in accordance with an aspect of the present invention.

Referring now to FIGS. 33 and 34, an implant 770 and corresponding insertion instrument 720 are shown. The insertion instrument 720 may be similar to the insertion instrument 700, as described in greater detail above, which will not be described again here for brevity sake. The insertion instrument 720 includes a body or handle portion 702, a top surface 704, a bottom surface 706, a side portion 708, a coupling member 710, a tapered portion 712, planar sections 716, an opening 722, and alignment markings 724. The alignment markings 724 show the position or angulation of the opening 722. The angulation of the opening 722 may correspond to the position or angulation of the second protrusion 786, as shown in FIG. 34. The implant 770 is a straight implant 770 with the first protrusion 784 aligned with the second protrusion 786, therefore, the opening 722 is a straight opening extending along the longitudinal axis of the insertion instrument 720. As the opening 722 is straight, the alignment markings 724 also extend along the planar sections 716 in a straight line positioned along the longitudinal axis of the insertion instrument 720.

The implant 770 includes a body portion or elongated cylindrical tube 772 with a first end 774 and a second end 776. The implant 770 also includes an inner elongated opening or canal 778 extending through the body portion 772 from the first end 774 to the second end 776. The elongated opening 778 may also include internal tapers extending radially inward from the first and second ends 774, 776. Although not shown, it is also contemplated that the implant 770 may be, for example, solid without an inner elongated opening 778 or include a first opening extending from the first end 774 into the body portion 772 to a point before the intermediate portion 788 of the implant 770 and a second opening extending from the second end 776 into the body portion 772 to a point before the intermediate portion 788 of the implant 770. The internal tapers of the implant 770 may be of the type described above with reference to internal tapers 110, 112 of implant 100, which will not be described again here for brevity sake. The first end 774 may also include an exterior tapered or angled edge 780 and the second end 776 may include an exterior tapered or angled edge 782.

The implant 770 may also include a first protrusion or first band of plasma sprayed material 784 extending circumferentially away from the body portion 772 near the first end 774 of the implant 770. The plasma sprayed material in the first band 784 may be, for example, titanium or another biocompatible material as known by one of ordinary skill in the art. The first protrusion or band 784 may fill a first circumferential groove or recess (not shown). The first circumferential groove or recess (not shown) may be of the type described above with reference to the first circumferential groove or recess 122 of implant 100, which will not be described again here for brevity sake. The implant 770 may further include a second protrusion or second band of plasma sprayed material 786 extending circumferentially away from the body portion 772 near the second end 776 of the implant 770. The plasma sprayed material in the first band 786 may be, for example, titanium or another biocompatible material as known by one of ordinary sill in the art. The second protrusion or band 786 may fill a second circumferential groove or recess (not shown). The second circumferential groove or recess (not shown) may be of the type described above with reference to the second circumferential groove or recess 124 of implant 100, which will not be described again here for brevity sake. The first protrusion 784 may have a first length and the second protrusion 786 may have a second length. The first length may be, for example, longer than the second length. The first and second protrusions or bands of plasma sprayed material 784, 786 may form, for example, a textured surface allowing for bone on-growth. It is also contemplated that the first and second protrusions 784, 786 may have, for example, a smooth exterior surface. The body 772 may include a portion, central member, intermediate portion, or intermediate region 788 positioned between the first protrusion 784 and the second protrusion 786. As shown in FIGS. 33 and 34, the portion 788 of the body 772 is aligned with the first and second protrusions 784, 786 to form a straight implant 770.

Referring now to FIGS. 35-38, another implant 800 is shown. The implant 800 may be used with the insertion instrument 700, as described in greater detail above and which will not be described again here for brevity sake. The implant 800 includes a body portion or elongated cylindrical tube or member 752 with a first end 754 and a second end 756. The implant 800 also includes a first opening 802 extending into the first end 754 and a second opening 804 extending into the second end 756. The first opening 802 may extend into the implant 800 from the first end 754 to an internal end 806. The internal end 806 may have, for example, a conical shape, pointed end, or tapered end. The second opening 804 may extend into the implant 800 from the second end 756 to an internal end 808. The internal end 808 may have, for example, a conical shape, pointed end, or tapered end. The openings 802, 804 may also include internal tapers 810, 812 extending radially inward from the first and second ends 754, 756. The internal tapers of implant 800 may be of the type described above with reference to internal tapers 110, 112 of implant 100, which will not be described again here for brevity sake. The first end 754 may also include an exterior tapered or angled edge 760 and the second end 756 may include an exterior tapered or angled edge 762.

Figure 35:
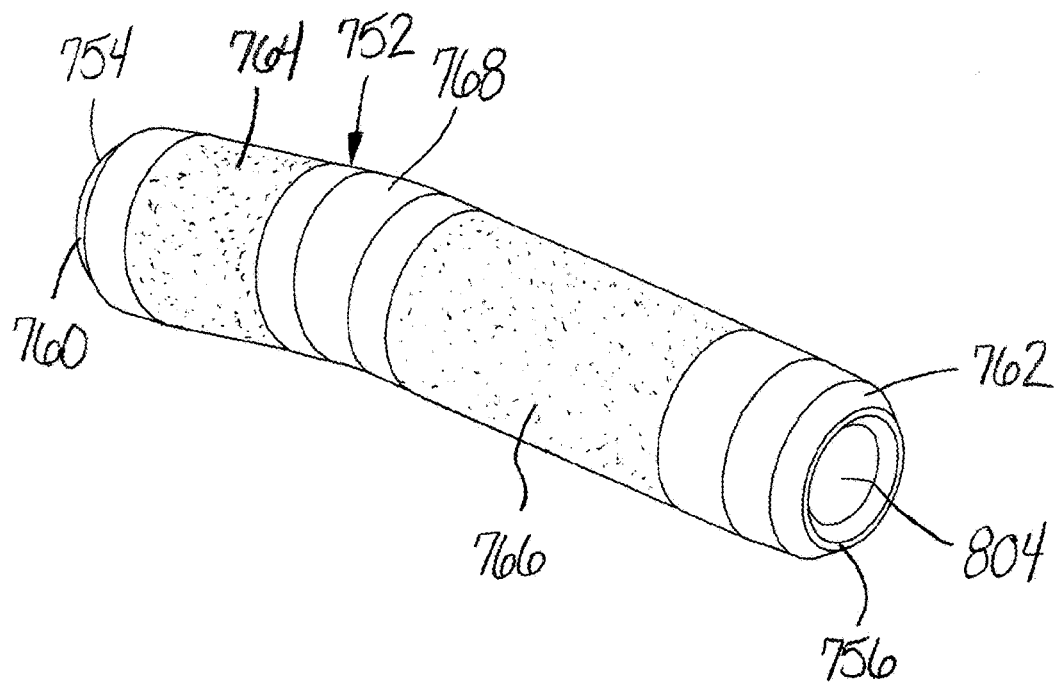
FIG. 35 is a perspective view of another embodiment of a bone implant, in accordance with an aspect of the present invention.
Figure 36:
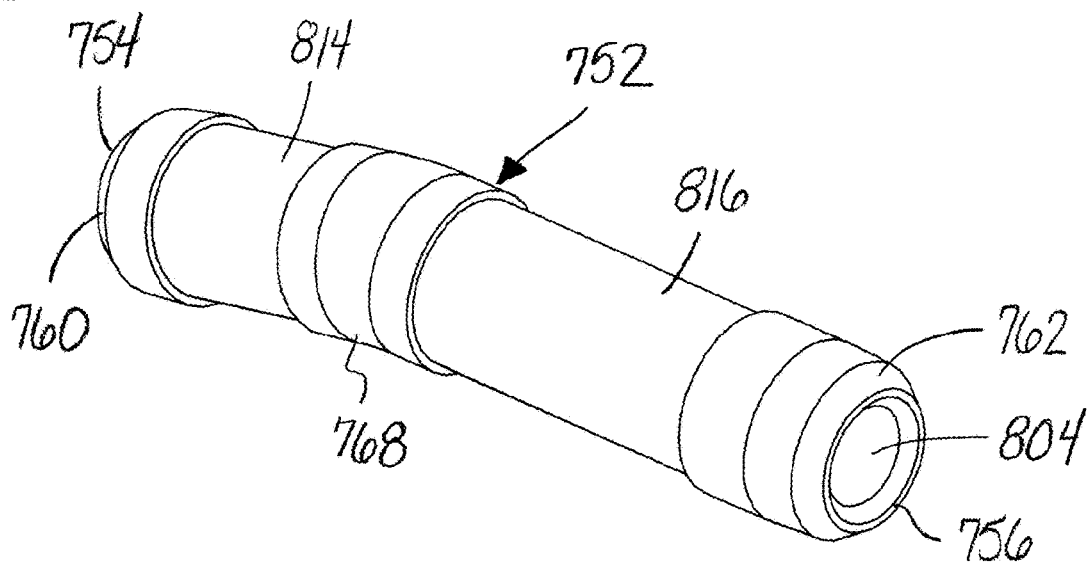
FIG. 36 is a perspective view of the bone implant of FIG. 35 without the plasma sprayed material, in accordance with an aspect of the present invention.
Figure 37:
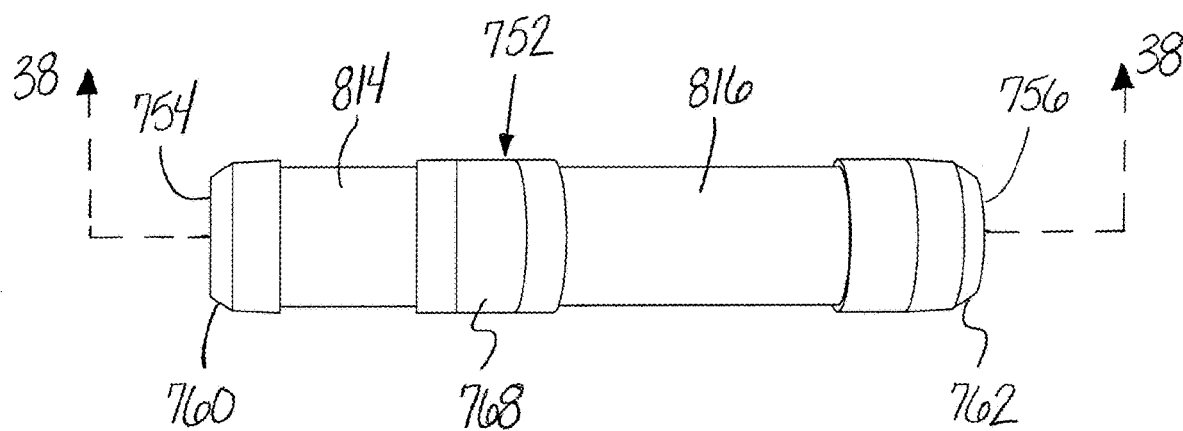
FIG. 37 is a top view of the bone implant of FIG. 35, in accordance with an aspect of the present invention.
Figure 38:
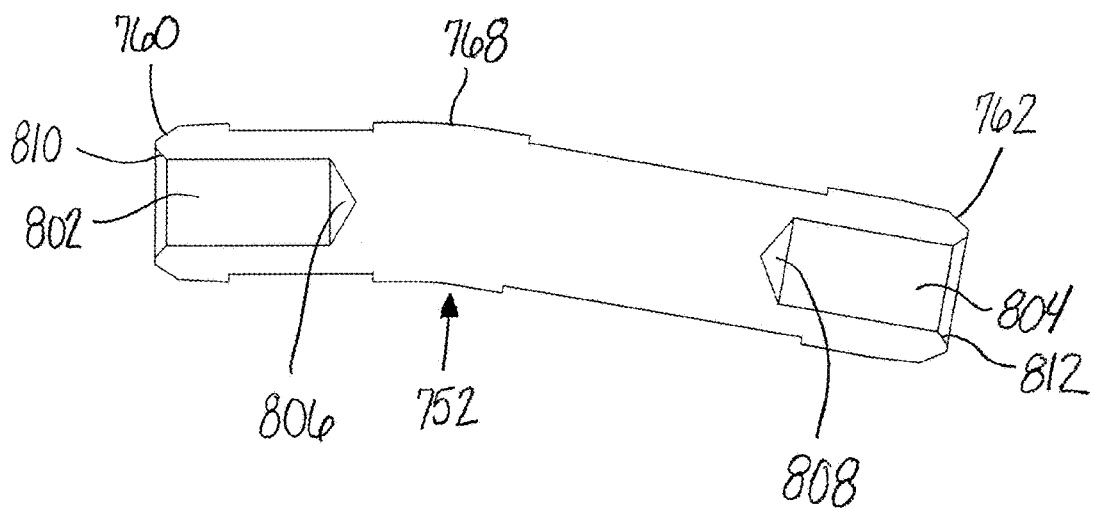
FIG. 38 is a cross-sectional view of the bone implant of FIG. 35 taken along line 38-38 in FIG. 37, in accordance with an aspect of the present invention.

The implant 800 may also include a first protrusion or first band of plasma sprayed material 764 extending circumferentially away from the body portion 752 near the first end 754 of the implant 800, as shown in FIG. 35. The plasma sprayed material in the first band 764 may be, for example, titanium or another biocompatible material as known by one of ordinary skill in the art. The first protrusion or band 764 may fill a first circumferential groove or recess 814, as shown in FIGS. 36-38. The first circumferential groove or recess 814 may be of the type described above with reference to the first circumferential groove or recess 122 of implant 100, which will not be described again here for brevity sake. The implant 800 may further include a second protrusion or second band of plasma sprayed material 766 extending circumferentially away from the body portion 752 near the second end 756 of the implant 800, as shown in FIG. 35. The plasma sprayed material in the second band 766 may be, for example, titanium or another biocompatible material as known by one of ordinary skill in the art. The second protrusion or band 766 may fill a second circumferential groove or recess 816, as shown in FIGS. 36-38. The second circumferential groove or recess 816 may be of the type described above with reference to the second circumferential groove or recess 124 of implant 100, which will not be described again here for brevity sake. The first protrusion 764 may have a first length and the second protrusion 766 may have a second length. The first length may be, for example, longer than the second length. The first and second protrusions or bands of plasma sprayed material 764, 766 may form, for example, a textured surface allowing for bone on-growth. It is also contemplated that the first and second protrusions 764, 766 may have, for example, a smooth exterior surface. The body 752 may include a portion, central member, intermediate portion, or intermediate region 768 positioned between the first protrusion 764 and the second protrusion 766. As shown in FIGS. 35, 36 and 38, the portion 768 of the body 752 is angled between the first and second protrusions 764, 766 to form an angled implant 800.

As may be recognized by those of ordinary skill in the art based on the teachings herein, numerous changes and modifications may be made to the above-described and other embodiments of the present disclosure without departing from the scope of the disclosure. The components of the instruments, implants, and/or systems as disclosed in the specification, including the accompanying abstract and drawings, may be replaced by alternative component(s) or feature(s), such as those disclosed in another embodiment, which serve the same, equivalent or similar purpose as known by those skilled in the art to achieve the same, equivalent or similar results by such alternative component(s) or feature(s) to provide a similar function for the intended purpose. In addition, the instruments, implants, and/or systems may include more or fewer components or features than the embodiments as described and illustrated herein. For example, the components and features of FIGS. 5 and 6, FIGS. 31 and 32, and FIGS. 35-38 may be used interchangeably and in alternative combinations as would be modified or altered by one of skill in the art. Accordingly, this detailed description of the currently-preferred embodiments is to be taken in an illustrative, as opposed to limiting of the disclosure.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components and/or groups thereof.

The corresponding structures, materials, acts, and equivalents of all means or step plus function elements in the claims below, if any, are intended to include any structure, material, or act for performing the function in combination with other claimed elements as specifically claimed. The description of one or more embodiments has been presented for purposes of illustration and description, but is not intended to be exhaustive or limited to in the form disclosed. Many modifications and variations will be apparent to those of ordinary skill in the art. The embodiment was chosen and described in order to best explain various aspects and the practical application, and to enable others of ordinary skill in the art to understand various embodiments with various modifications as are suited to the particular use contemplated.

What is claimed:

1. An implant insertion system, comprising:
   an insertion instrument with a first end and a second end, the insertion instrument comprising:
      an opening extending into the insertion instrument from the second end;
      a handle portion at the first end; and
      a coupling member at the second end, wherein the opening is positioned in the coupling member; and
   an implant comprising:
      a first portion at a first end;
      a second portion at a second end; and
      an intermediate portion coupling the first portion to the second portion;
      wherein the first portion is received within the opening of the insertion instrument and wherein the implant is a non-threaded implant.

2. The implant insertion system of claim 1, wherein the opening extends along a longitudinal axis of the insertion instrument.

3. The implant insertion system of claim 1, wherein the opening is angled relative to a longitudinal axis of the insertion instrument.

4. The implant insertion system of claim 1, wherein the insertion instrument further comprises:
   a tapered portion coupling the handle portion to the coupling member.

5. The implant insertion system of claim 1, wherein the insertion instrument further comprises:
   alignment markings positioned on sides of the coupling member, wherein the alignment markings comprise a plurality of dashes positioned in a straight line.

6. The implant insertion system of claim 5, wherein the alignment markings extend along a longitudinal axis of the insertion instrument.

7. The implant insertion system of claim 5, wherein the alignment markings are angled with respect to the insertion instrument.

8. The implant insertion system of claim 1, wherein the implant further comprises:
   an outer surface extending between the first end and the second end;
   a first circumferential recess formed in the outer surface of the first portion; and
   a second circumferential recess formed in the outer surface of the second portion;
   wherein the first circumferential recess extends between a position near the first end and a position near the second circumferential recess; and
   wherein the second circumferential recess extends between a position near the second end a position near the first circumferential recess.

9. The implant insertion system of claim 8, wherein the implant further comprises:
   a first band of plasma sprayed material disposed within the first recess and protruding radially outward beyond the outer surface of the first portion; and
   a second band of plasma sprayed material disposed within the second recess and protruding radially outward beyond the outer surface of the second portion.

10. The implant insertion system of claim 9, wherein the first band of plasma sprayed material protrudes radially outward 0.060 mm beyond the outer surface of the first portion and wherein the second band of plasma sprayed material protrudes radially outward 0.060 mm beyond the outer surface of the second portion.

11. The implant insertion system of claim 9, wherein the plasma sprayed material is titanium.

12. The implant insertion system of claim 9, wherein the outer surface of the first portion tapers radially outward from the first end towards the first circumferential recess.

13. The implant insertion system of claim 9, wherein the outer surface of the second portion tapers radially outward from the second end towards the second circumferential recess.

14. The implant insertion system of claim 9, wherein the implant further comprises:
   a first opening extending into the first portion from the first end toward the intermediate portion; and
   a second opening extending into the second portion from the second end toward the intermediate portion.

15. The implant insertion system of claim 9, wherein the implant includes an inner surface defining an elongated opening extending from the first end to the second end.

16. The implant insertion system of claim 15, wherein the inner surface tapers radially inward proximate the first end and proximate the second end.

17. The implant insertion system of claim 9, wherein the intermediate portion bends at an anatomically appropriate angle between the first band of plasma sprayed material and the second band of plasma sprayed material.

18. A method for inserting an implant into a first phalange and a second adjacent phalange so as to fuse the first phalange to the second phalange, said method comprising:
   providing an implant, the implant comprising:
      an elongated cylindrical member, the elongated cylindrical member including a first end, a second end and an outer surface extending between the first end and the second end, wherein a first circumferential recess is formed in the outer surface proximate the first end and a second circumferential recess is formed in the outer surface proximate the second end, wherein the first circumferential recess extends between the position proximate the first end and a position near the second circumferential recess and wherein the second circumferential recess extends between a position proximate the second end and a position near the first circumferential recess;
      a first band of plasma sprayed material disposed within the first recess and protruding radially outward beyond the outer surface of said elongated cylindrical member; and
      a second band of plasma sprayed material disposed within the second recess and protruding radially outward beyond the outer surface of said elongated cylindrical member;

inserting the first end of said elongated cylindrical member and at least a portion of the first band of plasma sprayed material of said implant into a bore formed in a distal end of the first phalange; and inserting the second end of said elongated cylindrical member and at least a portion of the second band of plasma sprayed material of said implant into a bore formed in a distal end of the second phalange.

19. The method of claim 18, wherein said elongated cylindrical member bends at an anatomically appropriate angle between said first band of plasma sprayed material and said second band of plasma sprayed material.

20. A method for an operative procedure for fusing a first phalange to a second adjacent phalange with an implant, said method comprising:

forming a bore in the first phalange;

forming a bore in the second phalange;

providing a first band of plasma sprayed material proximate a first end of said implant, wherein the implant is a non-threaded implant;

providing a second band of plasma sprayed material proximate a second end of said implant;

determining an appropriate angle between the first end to be positioned relative to the bore of the first phalange and the second end to be positioned relative to the bore of the second phalange during an operative procedure;

forming the determined angle in said implant between the first and second bands of plasma sprayed material;

inserting the first end and at least a portion of the first band of plasma sprayed material of said implant into the bore of the first phalange with an insertion instrument including a first end and a second end, the insertion instrument comprising:

an opening extending into the insertion instrument from the second end;

a handle portion at the first end; and a coupling member at the second end, wherein the opening is positioned in the coupling member; and inserting the second end and at least a portion of the second band of plasma sprayed material of said implant into the bore of the second phalange.

* * * * *